US012419933B2

(12) United States Patent
Haisser et al.

(10) Patent No.: US 12,419,933 B2
(45) Date of Patent: Sep. 23, 2025

(54) OPHTHALMIC COMPOSITION FOR THE TREATMENT OF UVEITIS

(71) Applicant: NOVALIQ GMBH, Heidelberg (DE)

(72) Inventors: Jörg Haisser, Siegelsbach (DE); Frank Löscher, Schriesheim (DE); Chiara Silvana Leo, Heidelberg (DE); Markus Beier, Weinheim (DE)

(73) Assignee: NOVALIQ GMBH, Heidelberg (DE)

( * ) Notice: Subject to any disclaimer, the term of this patent is extended or adjusted under 35 U.S.C. 154(b) by 576 days.

(21) Appl. No.: 17/640,679

(22) PCT Filed: Sep. 5, 2020

(86) PCT No.: PCT/EP2020/074884
§ 371 (c)(1),
(2) Date: Mar. 4, 2022

(87) PCT Pub. No.: WO2021/044045
PCT Pub. Date: Mar. 11, 2021

(65) Prior Publication Data
US 2023/0181679 A1 Jun. 15, 2023

(30) Foreign Application Priority Data
Sep. 6, 2019 (EP) ..................... 19195793

(51) Int. Cl.
| A61K 38/13 | (2006.01) |
| A61J 1/14 | (2023.01) |
| A61K 9/00 | (2006.01) |
| A61K 9/08 | (2006.01) |
| A61K 47/06 | (2006.01) |
| A61K 47/10 | (2017.01) |
| A61P 27/02 | (2006.01) |

(52) U.S. Cl.
CPC ............. *A61K 38/13* (2013.01); *A61J 1/1468* (2015.05); *A61K 9/0048* (2013.01); *A61K 9/08* (2013.01); *A61K 47/06* (2013.01); *A61K 47/10* (2013.01); *A61P 27/02* (2018.01)

(58) Field of Classification Search
None
See application file for complete search history.

(56) References Cited

U.S. PATENT DOCUMENTS

| 2,616,927 A | 11/1952 | Kauck et al. |
| 4,452,818 A | 6/1984 | Haidt |
| 4,649,047 A | 3/1987 | Kaswan |
| 5,077,036 A | 12/1991 | Long |
| 5,336,175 A | 8/1994 | Mames |
| 5,518,731 A | 5/1996 | Meadows |
| 5,667,809 A | 9/1997 | Trevino et al. |
| 5,874,469 A | 2/1999 | Maniar et al. |
| 5,874,481 A | 2/1999 | Weers et al. |
| 5,904,933 A | 5/1999 | Riess et al. |
| 5,980,936 A | 11/1999 | Krafft et al. |
| 5,981,607 A | 11/1999 | Ding et al. |
| 6,113,919 A | 9/2000 | Reiss et al. |
| 6,140,374 A | 10/2000 | May et al. |
| 6,262,126 B1 | 7/2001 | Meinert |
| 6,335,335 B2 | 1/2002 | Higashiyama et al. |
| 6,372,243 B2 | 4/2002 | Kobuch et al. |
| 6,458,376 B1 | 10/2002 | Meadows |
| 6,486,212 B2 | 11/2002 | Meinert |
| 6,489,367 B1 | 12/2002 | Meinert |
| 7,001,607 B1 | 2/2006 | Menz et al. |
| 7,026,359 B1 | 4/2006 | Gross et al. |
| 7,041,705 B2 | 5/2006 | Mishra et al. |
| 7,074,827 B2 | 7/2006 | Ueno |
| 7,258,869 B1 | 8/2007 | Berry et al. |
| 7,732,415 B2 | 6/2010 | Dawson et al. |
| 8,029,977 B2 | 10/2011 | Meinert et al. |
| 8,492,334 B2 | 7/2013 | Lavik et al. |
| 8,501,800 B2 | 8/2013 | Bowman et al. |
| 8,614,178 B2 | 12/2013 | Theisinger et al. |
| 8,669,241 B2 | 3/2014 | Matsumura et al. |
| 8,772,337 B2 | 7/2014 | Pilotaz et al. |
| 8,796,340 B2 | 8/2014 | Theisinger et al. |
| 8,865,131 B2 | 10/2014 | Hagedorn et al. |
| 8,957,110 B2 | 2/2015 | Aleo et al. |
| 8,986,738 B2 | 3/2015 | Meinert |
| 9,000,048 B2 | 4/2015 | Mecozzi et al. |
| 9,023,898 B2 | 5/2015 | Wong et al. |
| 9,241,900 B2 | 1/2016 | Wilson |
| 9,265,809 B2 | 2/2016 | Johnson |
| 9,278,120 B2 | 3/2016 | Cruzat et al. |
| 9,308,262 B2 | 4/2016 | Günther et al. |

(Continued)

FOREIGN PATENT DOCUMENTS

| EP | 0 670 159 A1 | 9/1995 |
| EP | 2 708 228 A1 | 3/2014 |

(Continued)

OTHER PUBLICATIONS

Murphy et al. Cyclosporine vs Tacrolimus Therapy for Posterior and Intermediate Uveitis. Arch Ophthalmol. 2005; 123(5):634-641. doi:10.1001/archopht.123.5.634 (Year: 2005).*
Babu et al., "Medical Management of Uveitis—Current Trends," Indian J Opthalmol., vol. 61, No. 6, p. 277-283, (2013).
Daull et al., "Distribution of Cyclosporine A in Ocular Tissues After Topical Administration of Cyclosporine A Cationic Emulsions to Pigmented Rabbits," Cornea, vol. 32, No. 3, p. 345-354, (2013); Abstract Only.
Dutescu et al., "Semifluorinated Alkanes as a Liquid Drug Carrier System for Topical Ocular Drug Delivery," European Journal of Pharmaceutics and Biopharmaceutics, vol. 88, No. 1, p. 123-128, (2014).

(Continued)

Primary Examiner — Christina Bradley
(74) Attorney, Agent, or Firm — Hoxie & Associates LLC

(57) ABSTRACT

The invention provides pharmaceutical compositions comprising cyclosporine dissolved in a semifluorinated alkane for use in the treatment of uveitis.

17 Claims, No Drawings

(56) References Cited

U.S. PATENT DOCUMENTS

| | | |
|---|---|---|
| 9,446,026 B2 | 9/2016 | Bingaman et al. |
| 9,757,459 B2 | 9/2017 | Theisinger et al. |
| 9,757,460 B2 | 9/2017 | Günther et al. |
| 9,770,508 B2 | 9/2017 | Günther et al. |
| 9,844,530 B1 | 12/2017 | Anastassov et al. |
| 9,878,000 B2 | 1/2018 | Gu et al. |
| 9,968,678 B2 | 5/2018 | Theisinger et al. |
| 10,004,714 B2 | 6/2018 | Zhu et al. |
| 10,045,996 B2 | 8/2018 | Theisinger et al. |
| 10,045,997 B2 | 8/2018 | Chen et al. |
| 10,058,615 B2 | 8/2018 | Günther et al. |
| 10,064,944 B2 | 9/2018 | Wilson |
| 10,130,707 B2 | 11/2018 | Günther et al. |
| 10,273,298 B2 | 4/2019 | Günther et al. |
| 10,286,035 B2 | 5/2019 | Gavaris |
| 10,369,117 B2 | 8/2019 | Günther et al. |
| 10,449,164 B2 | 10/2019 | Günther et al. |
| 10,507,132 B2 | 12/2019 | Graf et al. |
| 10,525,062 B2 | 1/2020 | Theisinger et al. |
| 10,555,953 B2 | 2/2020 | Theisinger et al. |
| 10,576,154 B2 | 3/2020 | Günther et al. |
| 10,682,315 B2 | 6/2020 | Scherer et al. |
| 10,813,976 B2 | 10/2020 | Löscher et al. |
| 10,813,999 B2 | 10/2020 | Günther et al. |
| 11,154,513 B2 | 10/2021 | Scherer et al. |
| 11,160,865 B2 | 11/2021 | Theisinger et al. |
| 11,241,497 B2 | 2/2022 | Reza et al. |
| 11,273,174 B2 | 3/2022 | Löscher et al. |
| 11,278,503 B2 | 3/2022 | Günther et al. |
| 11,285,163 B2 | 3/2022 | Shah et al. |
| 11,324,757 B2 | 5/2022 | Theisinger et al. |
| 11,357,738 B2 | 6/2022 | Scherer et al. |
| 11,400,132 B2 | 8/2022 | Löscher et al. |
| 11,413,323 B2 | 8/2022 | Leo et al. |
| 11,576,893 B2 | 2/2023 | Löscher et al. |
| 11,583,513 B2 | 2/2023 | Günther et al. |
| 11,684,589 B2 | 6/2023 | Günther et al. |
| 11,723,861 B2 | 8/2023 | Günther et al. |
| 11,844,836 B2 | 12/2023 | Günther et al. |
| 11,896,559 B2 | 2/2024 | Günther et al. |
| 12,005,033 B2 | 6/2024 | Günther et al. |
| RE50,060 E | 7/2024 | Graf et al. |
| 12,029,757 B2 | 7/2024 | Löscher et al. |
| 12,059,449 B2 | 8/2024 | Leo et al. |
| 12,128,010 B2 | 10/2024 | Scherer et al. |
| 12,150,955 B2 | 11/2024 | Löscher et al. |
| 12,226,422 B2 | 2/2025 | Löscher et al. |
| 2003/0018044 A1 | 1/2003 | Peyman |
| 2005/0079210 A1 | 4/2005 | Gupta |
| 2005/0175541 A1 | 8/2005 | Lanza et al. |
| 2008/0050335 A1 | 2/2008 | Faour et al. |
| 2010/0279951 A1 | 11/2010 | Morgan et al. |
| 2011/0223208 A1 | 9/2011 | Hill et al. |
| 2014/0004197 A1 | 1/2014 | Theisinger et al. |
| 2014/0186350 A1 | 7/2014 | Ghosh et al. |
| 2016/0000941 A1 | 1/2016 | Keller et al. |
| 2017/0087100 A1 | 3/2017 | Scherer et al. |
| 2017/0216204 A1 | 8/2017 | Theisinger et al. |
| 2017/0348285 A1 | 12/2017 | Hellstrom |
| 2018/0360908 A1 | 12/2018 | Beier et al. |
| 2019/0256591 A1 | 8/2019 | Günther et al. |
| 2019/0328717 A1 | 10/2019 | Günther et al. |
| 2019/0343793 A1 | 11/2019 | Günther et al. |
| 2020/0188318 A1 | 6/2020 | Günther et al. |
| 2021/0069014 A1 | 3/2021 | Löscher et al. |
| 2021/0121471 A1 | 4/2021 | Löscher et al. |
| 2021/0228595 A1 | 7/2021 | Löscher et al. |
| 2021/0315832 A1 | 10/2021 | Scherer et al. |
| 2021/0340248 A1 | 11/2021 | Günther et al. |
| 2021/0346313 A1 | 11/2021 | Beier et al. |
| 2022/0031844 A1 | 2/2022 | Mauden et al. |
| 2022/0079925 A1 | 3/2022 | Günther et al. |
| 2022/0143137 A1 | 5/2022 | Witt et al. |
| 2022/0152096 A1 | 5/2022 | Löscher et al. |
| 2022/0226426 A1 | 7/2022 | Löscher et al. |
| 2022/0226427 A1 | 7/2022 | Leo et al. |
| 2022/0354926 A1 | 11/2022 | Löscher et al. |
| 2022/0362382 A1 | 11/2022 | Löscher et al. |
| 2022/0370377 A1 | 11/2022 | Scherer et al. |
| 2023/0043641 A1 | 2/2023 | Beier et al. |
| 2023/0181679 A1 | 6/2023 | Haisser et al. |
| 2023/0330056 A1 | 10/2023 | Günther et al. |
| 2023/0398065 A1 | 12/2023 | Günther et al. |

FOREIGN PATENT DOCUMENTS

| | | | | |
|---|---|---|---|---|
| EP | 2 730 291 A1 | 5/2014 | | |
| GB | 2224205 A | 5/1990 | | |
| WO | WO 2007/008666 A2 | 1/2007 | | |
| WO | WO 2008/136034 A2 | 11/2008 | | |
| WO | WO 2011/073134 A1 | 6/2011 | | |
| WO | WO 2016/082644 A1 | 6/2016 | | |
| WO | 2018/033854 A1 | 2/2018 | | |
| WO | WO-2018114557 A1 * | 6/2018 | ........... | A61K 31/436 |
| WO | WO-2018115097 A1 * | 6/2018 | ................ | A61J 1/00 |

OTHER PUBLICATIONS

Prabhu et al., "Topical Cyclosporine A 0.05% for Recurrent Anterior Uveitis," Br J Opthalmol, vol. 100, No. 3, p. 345-347, (2016); Abstract Only.

"EvoTears, Product Description" Accessed Online: Dec. 21, 2023. https://evotears.com/at/das-produkt/ (Year: 2017).

"EvoTears—Gebrauchsanweisung," May 2015, retrieved from the Internet, date retrieved: Jun. 26, 2018, 2 pages, URL: http://video.apo-rot.de/docs/11213615.pdf.

"Keratoconjunctivitis," Cleveland Clinic, last updated Jul. 8, 2022, downloaded from https://my.clevelandclinic.org/health/diseases/23551-keratoconjunctivitis.

"Novaliq Announces Positive Topline Results of Phase 2 Clinical Trial Evaluating CyclASol® in Adults with Moderate to Severe Dry Eye Disease," Businesswire, Jan. 5, 2017, URL: <https://www.businesswire.com/news/home/20170105005211/en/Novaliq-Announces-Positive-Topline-Results-Phase-2>.

"Novaliq begins Phase 2 trial of Cyclasol for dry eye disease," Optometry Times, vol. 8, No. 3, (2016), p. 24.

"Novaliq GmbH Begins Phase II Clinical Trial of Cyclasol for the Treatment of Moderate to Severe Dry Eye Disease," (online), 5 pages, (2016); retrieved on Jan. 2021, from the Internet: https://www.biospace.com/article/releases/novaliq-gmbh-begins-phase-ii-clinical-trial-of-cyclasol-for-the-treatment-of-moderate-to-severe-dry-eye-disease-/.

"Ocular Surface Disease Index (OSDI)," Dec. 1, 2003, pp. 1-2, Retrieved from the Internet: URL: http://www.supereyecare.com/resources/OSDI.pdf.

"Semifluorinated alkane technology brings advantages for topical therapy," Ophthalmology Times, 2016, pp. 1-2.

"Topical drug dosage forms for eye conditions," The Pharmaceutical Journal, (Pharmaceutical Press, May 31, 2017), available at https://pharmaceutical-journal.com/article/Id/topical-drug-dosage-forms-for-eye-conditions.

"Xerophthalmia," Eye Clinic, 4 pages, archived Dec. 30, 2014.

Agarwal et al., "Modern Approaches to the Ocular Delivery of Cyclosporine A," Drug Discovery Today, vol. 21, No. 6, pp. 977-988, (2016); doi: 10.1016/j.drudis.2016.04.002.

Agrahari, et al., "A comprehensive insight on ocular pharmacokinetics," Drug Delivery and Translational Research, vol. 6, No. 6, pp. 735-754, (2016).

Ahmed, S. et al., "Ocular Drug Delivery: a Comprehensive Review," AAPS PharmSciTech, vol. 24, No. 66, pp. 1-29, (2023).

Ann Marie Griff, O.D., & Ann Pietrangelo, "Everything you need to know about keratoconjunctivitis," Healthline.com, Nov. 22, 2019, downloaded from https://www.healthline.com/health/keratoconjunctivitis.

Benezra, D. et al., "Cyclosporine eyedrops for the treatment of severe vernal keratoconjunctivitis," American Journal of Ophthalmology, vol. 101, pp. 278-282, (1986).

(56) References Cited

OTHER PUBLICATIONS

Bertilla et al., "Semifluorinated Alkanes as Stabilizing Agents of Fluorocarbon Emulsions," Springer, vol. 12, 24 pages, (2005).
Blackie et al., "Getting to the Root Cause of Dry Eye", Review of Optometry, pp. 1-12, (2012).
Bron, A. et al., "Grading of Corneal and Conjunctival Staining in the Context of Other Dry Eye Tests," Cornea, vol. 22, No. 7, pp. 640-650, (2003).
CEQUA® Prescribing Information, available at https://www.accessdata.fda.gov/drugsatfda_docs/label/2018/210913s000lbl.pdf(Aug. 2018) (last accessed Feb. 28, 2023).
Chaglasian, E. et al., "Recycling Cyclosporine," Review of Cornea & Contact Lenses, 2016, 5 pages.
Chao, W. et al., "Report of the Inaugural Meeting of the TFOS i2 = initiating innovation Series: Targeting the Unmet Need for Dry Eye Treatment," (London, United Kingdom, Mar. 21, 2015) Accepted Manuscript, Accepted Date: Nov. 11, 2015, 94 pages.
Chhadva et al., "Meibomian Gland Disease The Role of Gland Dysfunction in Drye Eye Disease," Ophthalmology, Vo. 124, No. 11 Supplement, pp. S20-S26, (2017).
Davies, N., "Biopharmaceutical Considerations in Topical Ocular Drug Delivery," Clinical and Experimental Pharmacology and Physiology, vol. 27, pp. 558-562, (2000).
Dembinski, R. et al., "Semi-fluorinated Alkanes as Carriers for Drug Targeting in Acute Respiratory Failure," Experimental Lung Research, vol. 36, pp. 499-507, (2010).
English-language machine translation of EP0670159 (A1) issued in U.S. Appl. No. 14/122,025 on Apr. 1, 2015, 10 pages.
Eva M. del Amo, "Topical ophthalmic administration: Can a drug instilled onto the ocular surface exert an effect at the back of the eye?" Frontiers in Drug Discovery 2:954771 (Sep. 8, 2022), available at https://www.frontiersin.org/articles/10.3389/fddev.2022.954771/full.
Gayton, J., "Etiology, Prevalence, and Treatment of Dry Eye Disease," Clinical Ophthalmology, vol. 3, pp. 405-412, (2009).
Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., vol. 255, No. 4, pp. 767-775, (2017).
Gehlsen, U., et al. "Cyclosporine A using F4H5 as liquid drug carrier is effective in treating experimental dry-eye disease," Investigative Ophthalmology & Visual Science, Abstract Only (2 pages) vol. 56, No. 7, p. 319, (2015).
Gehlsen, U., et al., "Omega-3 Fatty Acids Using F6H8-Carrier as Topical Therapy in Experimental Dry-Eye Disease," Investigative Ophthalmology & Visual Science, Abstract Only (1 page), vol. 57, pp. 417, (2016).
German, E.J., et al., "Reality of drop size from multi-dose eye drop bottles: is it cause for concern?" Eye, Vo. 13, pp. 93-100, (1999).
Gunther, B., "Breaking the Vicious Circle of Dry Eye Disease," OIS@ SECO, Feb. 21, 2019, pp. 1-14, New Orleans, URL: https://ois.net/wp-content/uploads/2019/02/DryEye-Novaliq.pdf.
Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).
Hardung, H., "Semifluorierte und perfluorierte Verbindungen zur topischen und parenteralen Anwendung," 2008, retrieved from http://www.freidok.uni-freiburg.de/volltexte/5682/pdf/Dissertation_Hardung.pdf (retrieved on Oct. 10, 2011).
Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, vol. 239, No. 5, pp. 373-381, (2001).
Holm, R. et al., "A novel excipient, 1-perfluorohexyloctane shows limited utility for the oral delivery of poorly water-soluble drugs," European Journal of Pharmaceutical Sciences, vol. 42, pp. 416-422, (2011).
IKERVIS® Prescribing Information, available at https://www.medicines.org.uk/emc/product/6937/smpc/print (Updated Mar. 2, 2022) (last accessed Apr. 27, 2023).
Kaercher et al., "NovaTears® as new Therapy in Dry Eye Results from three prospective, multicenter, non-interventional studies in different patient populations", TFOS Conference (Tear Film & Ocular Surface), Sep. 7-10, 2016, Montpellier, France, Poster Session II, Poster No. 60, 1 page.
Kumar, S. et al., "Reduction in drop size of ophthalmic topical drop preparations and the impact of treatment," J. Adv. Pharm. Tech. Res., vol. 2, No. 3, (2011).
Lallemand et al., "Cyclosporine A delivery to the eye: a pharmaceutical challenge," European Journal of Pharmaceutics and Biopharmaceutics, Abstract Only, 1 page, vol. 56, No. 3, pp. 307-318, (2003).
Lallemand et al., "Cyclosporine Delivery to the Eye: A comprehensive Review of Academic and Industrial Efforts," European Journal of Pharmaceutics and Biopharmaceutics, vol. 117, pp. 14-28, (2017).
Lemp, M., "Management of Dry Eye Disease," The American Journal of Managed Care, vol. 14, No. 3, pp. S88-S101, (2008).
Lin, H. et al., "Dry eye disease: A review of diagnostic approaches and treatments," Saudi Journal of Ophthalmology, vol. 28, pp. 173-181, (2014).
Majumdar, S. et al., "A Low Concentration of Tacrolimus/Semifluorinated Alkane (SFA) Eyedrop Suppresses Intraocular Inflammation in Experimental Models of Uveitis," Current Molecular Medicine, vol. 17, No. 3, pp. 211-220, (2017).
Meinert, H. et al., "Semifluorinated Alkanes—A New Class of Compounds with Outstanding Properties for Use in Ophthalmology," European Journal of Ophthalmology, vol. 10, No. 3, pp. 189-197, (2000).
Meinert, H. et al., "The Use of Semifluorinated Alkanes in Blood-Substitutes," Biomaterials, Artificial Cells, and Immobilization Biotechnology, vol. 21, No. 5, pp. 583-595, (1993).
Messmer, E.M., "The Pathophysiology, Diagnosis, and Treatment of Dry Eye Disease," Deutsches Arzteblatt International, vol. 112, No. 5, pp. 71-82, (2015).
Messmer, et al. "Semifluorierte Alkane als Therapie bei Meibomdrüsen-Dysfunktion Ergebnisse einer prospektiven, multizentrischen Beobachtungsstudie," DOG-Kongress, Sep. 29-Oct. 2, 2016, Berlin DOG (Deutsche Ophtalmologische Gesellschaft), Poster PSa03-02, (German language version).
Messmer, et al. "Semifluorinated Alkanes as a Therapy for Meibomian Gland Dysfunction Results of a prospective, multi-centered observational study," DOG-Kongress, Sep. 29-Oct. 2, 2016, Berlin DOG (Deutsche Ophtalmologische Gesellschaft), Ophthalmologe, Aug. 2016, Poster PSa03-02, English Abstract, p. 138.
Messmer, et al. "Semifluorinated Alkanes as a Therapy for Meibomian Gland Dysfunction Results of a prospective, multi-centered observational study," Presentation, DOG-Kongress, Sep. 29-Oct. 2, 2016, Berlin DOG (Deutsche Ophtalmologische Gesellschaft), Poster: PSa03-02, English Translation, 6 pages.
Miller, K. et al., "Minimal Clinically Important Difference for the Ocular Surface Disease Index," Socioeconomics and Health Services, Arch Ophthalmol, vol. 128, No. 1, pp. 94-101, (2010).
Murphy, C. et al., "Cyclosporine vs Tacrolimus Therapy for Posterior and Intermediate Uveitis," Arch Ophthalmol., vol. 123, pp. 634-641, (2005).
O'Rourke, M. et al., "Enhancing Delivery of Topical Ocular Drops," Cataract & Refractive Surgery Today Europe, 2016, 2 pages.
Perry, H., "Dry Eye Disease: Pathophysiology, Classification, and Diagnosis," The American Journal of Managed Care, vol. 14, No. 3, pp. S79-S87, (2008).
Pflugfelder et al., "The Pathophysiology of Dry Eye Disease What We Know and Future Directions for Research," Ophthalmology, vol. 124, No. 11 Supplement, pp. S4-S13, (2017).
Qiao, J. et al., "Emerging treatment options for meibomian gland dysfunction," Clinical Ophthalmology, vol. 7, pp. 1797-1803, (2013).
RESTASIS® Prescribing Information, available at https://www.accessdata.fda.gov/drugsatfda_docs/label/2012/050790s020lbl.pdf(Nov. 2012) (last accessed Feb. 28, 2023).

(56) References Cited

OTHER PUBLICATIONS

Sall, K. et al., "Two Multicenter, Randomized Studies of the Efficacy and Safety of Cyclosporine Ophthalmic Emulsion in Moderate to Severe Dry Eye Disease," Ophthalmology, vol. 107, No. 4, pp. 631-639, (2000).
Scherer et al., "Eyesol: A Novel Topical Ocular Drug Delivery System for Poorly Soluble Drugs," Drug Development & Delivery, vol. 13, No. 1, pp. 40-44, (2013).
Schmutz et al., "Fluorinated Vesicles Made from Combinations of Phospholipids and Semifluorinated Alkanes. Direct Experimental Evidence of the Location of the Semifluorinated Alkane within the Bilayer", Langmuir, vol. 19, pp. 4889-4894, (2003).
Sheppard, J. et al., "A Water-free 0.1% Cyclosporine A Solution for Treatment of Dry Eye Disease: Results of the Randomized Phase 2B/3 Essence Study," Cornea, vol. 40, No. 10, pp. 1290-1297, (2021).
Spöler et al., "Towards a New in vitro Model of Dry Eye: The ex vivo Eye Irritation Test," Developments in Ophthalmology, vol. 45, pp. 93-107, (2010).
Steven et al., "Semifluorinated Alkane Eye Drops for Treatment of Dry Eye Disease Due to Meibomian Gland Disease," Journal of Ocular Pharmacology and Therapeutics, vol. 33, No. 9, pp. 1-8, (2017).
Steven, P. et al. "Semifluorinated Alkane Eye Drops for Treatment of Dry Eye Disease—A Prospective, Multicenter Noninterventional Study" Journal of Ocular Pharmacology and Therapeutics, vol. 31, No. 8, pp. 498-503, (2015).
Steven, P. et al., "Semifluorinated Alkane Eye Drops for Treatment of Dry Eye Disease—A Prospective, Multicenter Noninterventional Study," Investigative Ophthalmology & Visual Science, vol. 56, p. 4493, (2015), Abstract Only.
Torkildsen, G. et al., "A Clinical Phase 2 Study to Assess Safety, Efficacy, and Tolerability of CyclASol for the Treatment of Dry Eye Disease," Poster Presentation at American Academy of Ophthalmology (AAO), New Orleans, (2017).
Wirta, David L. et al., "A Clinical Phase II Study to Assess Efficacy, Safety and Tolerability of Waterfree Cyclosporine Formulation for the Treatment of Dry Eye Disease," Ophthalmology, vol. 126, pp. 792-800, (2019).
Wong, D. et al., "Perfluorocarbons and Semifluorinated Alkanes," Seminars in Ophthalmology, vol. 15, No. 1, pp. 25-35, (2000).
Xalatan, Latanoprost Ophthalmic Solution, 50 µg/mL Prostaglandin F 2α analogue, Product Monograph, Jul. 21, 2014, 30 pages.
Yaoxue Zhuanye Zhishi II (Editor: Jin Xiangqun), Military Medical Science Press, 1st Printing of 2nd Edition, Mar. 2009, p. 158.
Yaoxue Zhuanye Zhishi II (Editor: Jin Xiangqun), Military Medical Science Press, 1st Printing of 2nd Edition, Mar. 2009, p. 158, 3 pages (English Machine Translation).
Zeng, Y., "Atlas of Clinical Keratoconjunctival Disease," Hubei Science and Technology Press, pp. 287-299, (2011).
Zeng, Y., "Atlas of Clinical Keratoconjunctival Disease," Hubei Science and Technology Press, pp. 287-299, (2011), English Translation.
Zhang, X. et al., "Dry Eye Management: Targeting the Ocular Surface Microenvironment," International Journal of Molecular Sciences, vol. 18, pp. 1398, 28 pages, (2017).
"PharmaNews," Kompass Ophthalmologie, vol. 2, No. 2, pp. 98-99, (2016).
Agarwal, P. et al., "Semifluorinated alkane based systems for enhanced corneal penetration of poorly soluble drugs," International Journal of Pharmaceutics, vol. 538, No. 1-2, pp. 119-129, (2018).
English language machine translation for "PharmaNews," Kompass Ophthalmologie, vol. 2, No. 2, pp. 98-99, (2016).
Pensyl, D., "Chapter 14: Preparations for Dry Eye and Ocular Surface Disease," Clinical Ocular Pharmacology, Fifth Edition, pp. 263-278, 18 pages, (2008).
Utine, C. et al., "Clinical Review: Topical Ophthalmic Use of Cyclosporin A," Ocular Immunology & Inflammation, vol. 18, No. 5, pp. 352-361, (2010).

\* cited by examiner

OPHTHALMIC COMPOSITION FOR THE TREATMENT OF UVEITIS

CROSS-REFERENCE TO RELATED APPLICATIONS

This application is a U.S. National Stage application under 35 U.S.C. § 371 of International Application No. PCT/EP2020/074884, filed on Sep. 5, 2020, which claims priority to and the benefit of European Application No. 191915793.5, filed on Sep. 6, 2019, the contents of each of which are hereby incorporated by reference in their entireties.

DESCRIPTION

Background of the Invention

Uveitis is an inflammation of the uvea, the middle layer of the eye. Located between the sclera, the eye's white outer coat, and the inner layer of the eye, called the retina, the uvea consists of the iris, ciliary body and choroid.

Depending on which part of the eye is affected, uveitis is classified in: uveitis at the front of the eye (anterior uveitis), which can cause redness and pain; uveitis in the middle of the eye (intermediate uveitis), which can cause floaters and blurred vision; uveitis at the back of the eye (posterior uveitis), which can cause vision problems. Uveitis can sometimes affect both the front and the back of the eye and this is known as panuveitis.

Uveitis at the front of the eye is the most common type of uveitis, accounting for about three out of four cases. Localized primarily in the anterior segment of the eye, anterior uveitis includes iritis (inflammation in the anterior chamber alone) and iridocyclitis (inflammation in the anterior chamber and anterior vitreous). Posterior uveitis generally refers to chorioretinitis. The inflammatory products (i.e. cells, fibrin, excess proteins) of these inflammations are commonly found in the fluid spaces of the eye, i.e. anterior chamber, posterior chamber and vitreous space as well as infiltrating the tissue imminently involved in the inflammatory response.

Uveitis can also be described according to how long it lasts: acute uveitis, in case it develops quickly and improves within three months; recurrent uveitis, where there are repeated episodes of inflammation separated by gaps of several months; chronic uveitis, where the inflammation lasts longer and returns within three months of stopping treatment.

Uveitis is further classified according to etiological criteria in three main categories: infectious (e.g. bacterial, viral, fungal); non-infectious (e.g. known systemic associations, no known systemic association); masquerade (e.g. neoplastic).

Corticosteroids and immunosuppressive agents are described as treatment options for uveitis. Topical administration of steroids is accompanied by side effects like increase of the intraocular pressure, susceptibility to infections, impaired corneal and scleral wound healing, corneal epithelial toxicity and crystalline keratopathy. It is important that patients on topical corticosteroids be regularly monitored to assess the response to therapy as well as development of side effects. The commonly available topical corticosteroids preparations are reported in the table below.

| Medication | Concentration (%) | Formulation |
|---|---|---|
| Dexamethasone sodium phosphate | 0.1 | Solution |
| Dexamethasone alcohol | 0.1 | Suspension |
| Fluorometholone acetate | 0.1 | Suspension |
| Fluorometholone alcohol | 0.1-0.125 | Suspension |
| Loteprednol | 0.2-0.5 | Suspension |
| Betamethasone phosphate | 0.1-0.5 | Solution |
| Prednisolone acetate (LS) | 0.12-0.125 | Suspension |
| Prednisolone acetate | 1 | Suspension |
| Prednisolone sodium phosphate | 0.125-1 | Solution |
| Difluprednate | 0.05 | Emulsion |
| Rimexolone | 1 | Suspension |

Immunosuppressive drugs can be classified as antimetabolites, T cell inhibitors, and alkylating agents. The antimetabolites include methotrexate, azathioprine, and mycophenolate mofetil. The T cell inhibitors include cyclosporine, tacrolimus, voclosporin, and sirolimus. The alkylating agents include cyclophosphamide and chlorambucil. Systemic administration of cyclosporine (Sandimmune®, Neoral) at a dose of 2.5-5 mg/kg/day is associated with renal dysfunction, tremor, hirsutism, hypertension, gum hyperplasia. Further, immunosuppressive drugs may take many weeks to have an effect, so initial therapy of ocular inflammation typically include high dose of systemic steroids. Immunosuppressive therapy can be started simultaneously with corticosteroids in severe cases or during the tapering of oral corticosteroids 4-8 weeks later in cases of chronic uveitis (K. Babu et al., *Indian J. Ophthalmol.;* 2013 June; 61(6):277-283).

Cyclosporins have been used to treat inflammatory conditions. Cyclosporine is available, at least in the US as an approved medicine in the form of an ophthalmic (o/w) emulsion (Restasis®). This product is indicated to increase tear production in patients whose tear production is presumed to be suppressed due to ocular inflammation associated with keratoconjunctivis sicca.

Prabhu S S et al., *Br. J. Ophthalmol.* 2016; 100:345-347, describe the results of a study in which topical cyclosporine A emulsion 0.05% is administered for the treatment of anterior uveitis to patients while on conventional treatment.

Daull et al. in *Cornea*, Volume 32, Number 3, March 2013, describe a study in which the ocular and systemic distribution of cyclosporine A (CsA) in rabbits after the instillation of preservative free cyclosporine cationic and anionic emulsions was compared with Restasis®.

U.S. Pat. No. 4,649,047 describes a study in which cyclosporine in olive oil is administered to rabbits' eyes. The levels of cyclosporine found in the different ocular tissues is described.

WO2011/073134 A1 describes pharmaceutical compositions in the form of solutions comprising cyclosporine and a semifluorinated alkane as a liquid vehicle which may be administered to the eye of a patient, such as for the treatment of keratoconjunctivitis sicca, for instance compositions comprising cyclosporine in semifluorinated alkane 1-perfluorobutyl-pentane (F4H5) in the presence of ethanol as a co-solvent. WO2011/073134 A1 however does not describe treatement of uveitis.

It is thus an object of the present invention to provide pharmaceutical compositions for use in the treatment of uveitis and associated conditions which offer a steroid free treatment to patients, thus avoiding steroid related side effects and the regular monitoring required with said treatments. Further objects of the invention will be clear on the basis of the following description of the invention, examples and claims.

SUMMARY OF THE INVENTION

In a first aspect, the invention relates to a pharmaceutical composition for use in the treatment of uveitis, wherein the composition comprises cyclosporine in 1-perfluorobutyl-pentane. In yet a further aspect, the invention provides for a kit comprising a pharmaceutical composition for such uses, wherein the kit comprises a container for holding the pharmaceutical composition and a drop dispenser adapted for administering about 8 to 12 µl volume of the composition per drop.

DETAILED DESCRIPTION OF THE INVENTION

The present invention relates to, in a first aspect, a pharmaceutical composition for use in a method of treating uveitis or a disease or condition associated thereto, wherein the composition comprises cyclosporine at a concentration of from about 0.05% (w/v) to 0.5% (w/v) and 1-perfluorobutyl-pentane.

Uveitis is the inflammation of the uvea. The inflammatory products of this inflammation are commonly found in the fluid spaces of the eye, like for example the anterior chamber, the posterior chamber and the vitreous space. Uveitis disrupts vision by primarily causing problems with the lens, retina, optic nerve, and vitreous. Uveitis can affect one or both eyes. Symptoms may develop rapidly and can include: blurred vision, dark, floating spots in the vision (floaters), eye pain, redness of the eye, sensitivity to light (photophobia).

Posterior uveitis primarily occurs in the back of the eye, often involving both the retina and the choroid. It is often called choroditis or chorioretinitis. Anterior uveitis means an inflammation of the iris (iritis) or the iris and the ciliar body (iridocyclitis). The term "intermediate uveitis" is used for that subset of uveitis where the vitreous is the major site of the inflammation and if there is an associated infection (for example, Lyme disease) or systemic disease (for example, sarcoidosis)

In a preferred embodiment of the present invention, uveitis is one selected from anterior uveitis and posterior uveitis. In a more preferred embodiment, uveitis is anterior uveitis.

Cyclosporine (synonyms include cyclosporin A, CsA, or ciclosporin) is a cyclic nonribosomal peptide comprising 11 amino acids with the empirical formula $C_{62}H_{111}N_{11}O_{12}$ and molecular weight of 1202.61. It is an immunosuppressant drug that is widely used in post-allergenic organ transplant, to reduce the activity of the patient's immune system and thereby, the risk of organ rejection. Cyclosporine is typically provided as a colourless or white powder.

Cyclosporine is thought to bind to the cytosolic protein cyclophilin (immunophilin) of immunocompetent lymphocytes, especially T-lymphocytes. This complex of cyclosporin and cyclophilin inhibits calcineurin, which, under normal circumstances, is responsible for activating the transcription of interleukin 2. It also inhibits lymphokine production and interleukin release and, therefore, leads to a reduced function of effector T-cells.

Cyclosporine is a pharmacological treatment option for dry eye disease, which is available as a prescription medication, for example in the US in the form of an 0.05% ophthalmic (o/w) emulsion (Restasis®). This product is indicated to increase tear production in patients whose tear production is presumed to be suppressed due to ocular inflammation associated with keratoconjunctivis sicca. Restasis® is administered twice a day in each eye approximately 12 hours apart. It is packaged in single-vials. (Prescribing Information, Restasis®).

Preferably, the pharmaceutical composition for the use of the present invention is formulated as a solution, even more preferred as a clear solution.

The term a "clear solution", as mentioned above and understood herein, refers to a liquid solution in which all solutes are fully dissolvable or dissolved under room temperature conditions i.e. between 15 and 25° C. The clear solution does not comprise of any particulate or solid phase components and preferably has a refractive index approximate to that of water (i.e. 1.333) at room temperature.

In the present invention, the pharmaceutical composition comprises 1-perfluorobutyl-pentane, with the chemical formula $F(CF_2)_4(CH_2)_5H$. It is an inert, water-insoluble liquid, with a density of 1.284 g/cm$^3$ at 25° C. and refractive index of 1.3204 at 20° C. Alternative nomenclature for this compound includes F4H5, wherein F denotes a linear perfluorinated alkane segment comprising 4 carbon atoms and wherein H denotes a linear and non-fluorinated alkane segment of 5 carbon atoms. Preferably, the 1-perfluorobutyl-pentane is substantially free of water.

The pharmaceutical composition for the use of the present invention may comprise from about 95 to about 99% wt.-%, more preferably from about 98 to about 99% wt.-%, of 1-perfluorobutyl-pentane as described above, based on the total weight of the composition.

The pharmaceutical composition for use according to the present invention may comprise at least about 97% (w/w), preferably at least about 98% (w/w), more preferably at least about 99% (w/w) of 1-perfluorobutyl-pentane, based on the total weight of the pharmaceutical composition.

In another embodiment, the pharmaceutical composition according to the present invention may optionally further comprise 2-perfluorobutyl-pentane. Preferably the composition, in addition to 1-perfluorobutyl-pentane, may optionally comprise minor amounts of 2-perfluorobutyl-pentane of up to 2% (w/w), preferably up to 1% (w/w), more preferably of up to 0.5% (w/w).

The concentration of cyclosporine in the pharmaceutical composition for use according to the invention is in the range of from 0.05% (w/v) to about 0.5% (w/v) with respect to the total volume of the composition, preferably in the range of from about 0.05% to 0.3% (w/v), more preferably in the range of from 0.05% to 0.2% (w/v). In a preferred embodiment, the concentration of cyclosporine in the pharmaceutical composition for use according to the invention is in the range of about 0.05 to 0.1% (w/v), more preferably about 0.05% (w/v) or about 0.1% (w/v).

Unless otherwise indicated, the term "% (w/v)" denotes the amount of a component of a composition as a weight percentage in relation to the total volume of the composition (with 'w' denoting the weight and 'v' denoting volume). For example 0.05% (w/v) may be understood as relating to 0.5 mg of a component in 1 mL of the composition, and 0.1% (w/v) would correspond to 1.0 mg of a component in 1 mL of the composition. Unless otherwise indicated, the term "% (w/w)" refers to the amount of a component of a composition as a weight percentage in relation to the total weight of the composition (with 'w' denoting weight).

The term 'about' as used herein and in reference or connection to a parameter, for example such as the concentration of cyclosporine dissolved in the composition or the amount of cyclosporine featured in a single dose of the composition includes the precise value as defined, as well as any value falling within the degree of variability usually observed in measuring or determining these parameters using the standard techniques and equipment known in the art and field.

A single dose of the pharmaceutical composition for the use of the present invention may be administered in a volume of about 8-12 µl, preferably in a volume of about 10-12 µl, more preferably 11-12 µl, most preferably about 11 µl.

A dose of a composition for use according to the present invention and as described in any one of the embodiments herein is preferably topically administered in the form of a (i.e. one) single drop to an eye of a subject. The drop may be administered to the surface of the eye, preferably to any surface region or tissue of the eye that is accessible to topical administration or instillation, for example to the cornea or conjunctiva. The single drop of the composition may be instilled directly onto a surface of the eye, such as the corneal surface of the eye, or alternatively into a space i.e. sac or pocket formed by gently pulling down of the lower eyelid of an eye.

As used herein, the term 'administration to an eye' or 'per eye' refers to the administration of a given dose, e.g. a single dose, of a pharmaceutical composition according to the invention to an individual eye of a subject. The therapy of the uveitis and diseases or associated conditions as described herein however, should be understood as being not limited to the treatment of a single eye in a subject, but as being also inclusive of a therapy involving the administration of composition according to the present invention to each i.e. both eyes of a subject which are affected by uveitis.

In the present invention, the pharmaceutical composition may also comprise one or more further excipients as an optional and additional component. The term "excipients" as used herein refers to any pharmaceutically acceptable natural or synthetic substance that may be added to the pharmaceutical composition to enhance or otherwise modify its physical or chemical constitution or stability or therapeutic properties. The present pharmaceutical composition may optionally comprise one or more excipients such as, for example, an antioxidant, a preservative, a lipid or oily excipient, a surfactant or a lubricant or a combination of at least 2 excipients thereof.

Suitable antioxidants for use in the present pharmaceutical composition comprise, for example: butylated hydroxytoluene (BHT), butylated hydroxyanisole (BHA), tertiary butylhydroquinone (TBHQ), vitamin E, vitamin E derivatives (i.e. alpha-tocopherol acetate) or ascorbic acid.

Suitable lipid or oily excipients for use in the pharmaceutical composition of the present invention comprise, for example, triglyceride oils (i.e. soybean oil, olive oil, sesame oil, cotton seed oil, castor oil, sweet almond oil), triglycerides, mineral oil (i.e. petrolatum and liquid paraffin), medium chain triglycerides (MCT), oily fatty acids, isopropyl myristate, oily fatty alcohols, esters of sorbitol and fatty acids, oily sucrose esters, or any other oily substance which is physiologically tolerated by the eye.

Suitable lubricants for use in the pharmaceutical composition of the present invention comprise, for example, carboxymethylcellulose and its sodium salt (CMC, carmellose), polyvinyl alcohol, hydroxypropyl methylcellulose (HPMC, hypromellose), hyaluronic acid and its sodium salt, or hydroxypropyl guar gum.

The pharmaceutical composition according to the present invention may or may not comprise pharmaceutically suitable natural or synthetic preservatives, such as, for example, benzalkonium chloride and chlorhexidine. In a preferred embodiment, however, the pharmaceutical composition according to the present invention does not comprise a pharmaceutically acceptable preservative.

In addition to the excipients as described above as optional components, the present pharmaceutical composition may also comprise one or more further solvents.

The term "further solvents" as used herein refers to a solvent or mixture of two or more different solvents other than 1-perfluorobutyl-pentane. Suitable further solvents may be chosen from, for example, alcohols, such as ethanol, isopropanol or other further solvent which is physiologically tolerated by the eye.

Ethanol may be present in the pharmaceutical composition for use according to the present invention in an amount of up to about 1.0 wt.-%, such as, for example from 0.2 to 1.0 wt.-% (corresponding to 0.2% to 1.0% (w/w)) or 0.5 to 1.0 wt.-% (corresponding to 0.5 to 1.0% (w/w)), based on the total weight of the composition (final dosage form). Preferably, the pharmaceutical composition for use according to the present invention comprises about 0.5 to 1.0 wt.-% ethanol, more preferably about 1.0 wt.-% ethanol with respect to the total weight of the pharmaceutical composition.

In a preferred embodiment, the pharmaceutical composition for the use of the present invention is essentially free of water, whereas the residual water may be attributed to the potential residual water content of cyclosporin. The term 'essentially' as used herein means if present then in trace or residual amounts such as to confer no technical advantage or relevance in respect of the object of the invention.

As used herein, the term "up to about" or "up to" used in context of a parameter, such as presently in relation to the amount of ethanol in the composition, refers to any value of the parameter greater than zero and up to, and inclusive of, the defined parameter. For example, an amount of "up to about 1.0% (w/w) of ethanol" should be understood as including any value greater than zero ranging up to and including the value of 1.0% (w/w) of ethanol, and would include, for example, values such as 0.01%, 0.05%, 0.1%, 0.2%, 0.3%, 0.4%, 0.5% 0.6%, 0.7, 0.8, 0.9, 0.95%, 0.99% (w/w) of ethanol, taking into account any degree of variability usually observed in measuring or determining this parameter, using the standard techniques and equipment known in the relevant field.

In another preferred embodiment, the pharmaceutical composition for the use of the present invention is (essentially) water-free and/or preservative free.

In one embodiment of the invention, the composition for the use according to the invention may comprise about 0.05% to 0.1% (w/v) cyclosporine dissolved in 1-perfluorobutyl-pentane, and about 1.0% (w/w) of ethanol based on the total weight of the composition.

In another embodiment, the pharmaceutical composition for the use of the present invention consists essentially of about 0.05% to 0.1% (w/v) cyclosporine dissolved in 1-perfluorobutyl-pentane. In another embodiment, the pharmaceutical composition for the use of the present invention consists essentially of about 0.05% to 0.1% (w/v) cyclosporine dissolved in 1-perfluorobutyl-pentane and about 1.0% (w/w) ethanol based on the total weight of the composition.

In preferred embodiments of the invention, the composition for use as described herein may preferably comprise, or consist of:

0.05 to 0.1% (w/v) of cyclosporine dissolved in 1-perfluorobutyl-pentane and 0.5% (w/w) ethanol, or
0.05 to 0.1% (w/v) of cyclosporine dissolved in 1-perfluorobutyl-pentane and 1.0% (w/w) ethanol, or
0.05% (w/v) cyclosporine dissolved in 1-perfluorobutyl-pentane and 0.5% (w/w) ethanol, or
0.1% (w/v) cyclosporine dissolved in 1-perfluorobutyl-pentane and 0.5% (w/w) ethanol, or
0.1% (w/v) cyclosporine dissolved in 1-perfluorobutyl-pentane and 1.0% (w/w) ethanol, or
0.05% (w/v) cyclosporine dissolved in 1-perfluorobutyl-pentane and 1.0% (w/w) ethanol, or
0.05 to 0.1% (w/v) of cyclosporine dissolved in 1-perfluorobutyl-pentane, or
0.1% (w/v) cyclosporine dissolved in 1-perfluorobutyl-pentane, or
0.05% (w/v) cyclosporine dissolved in 1-perfluorobutyl-pentane, or
0.05 to 0.5% (w/v) cyclosporine dissolved in 1-perfluorobutylpentane and 1.0% (w/w) ethanol, or
0.05 to 0.5% (w/v) cyclosporine dissolved in 1-perfluorobutylpentane, or
0.1 to 0.5% (w/v) cyclosporine dissolved in 1-perfluorobutylpentane and 1.0% (w/w) ethanol, or
0.1 to 0.5% (w/v) cyclosporine dissolved in 1-perfluorobutylpentane, or
0.1 to 0.3% (w/v) cyclosporine dissolved in 1-perfluorobutylpentane and 1.0% (w/w) ethanol, or
0.1 to 0.3% (w/v) cyclosporine dissolved in 1-perfluorobutylpentane, or
0.05 to 0.5% (w/v) cyclosporine dissolved in 1-perfluorobutylpentane and 0.5% (w/w) ethanol, or
0.1 to 0.5% (w/v) cyclosporine dissolved in 1-perfluorobutylpentane and 0.5% (w/w) ethanol, or
0.1 to 0.3% (w/v) cyclosporine dissolved in 1-perfluorobutylpentane and 0.5% (w/w) ethanol.

In a preferred embodiment, the pharmaceutical composition for the use of the present invention is a clear solution comprising cyclosporin at a concentration of from about 0.05% (w/v) to 0.5% (w/v), preferably from about 0.05% (w/v) to 0.3% (w/v), more preferably from about 0.05% (w/v) to 0.2% (w/v), most preferably from 0.05% (w/v) to 0.1% (w/v) dissolved in 1-perfluorobutyl-pentane and up to about 1% (w/w) ethanol (at room temperature conditions i.e. between 15 to 25° C.). In a preferred embodiment, the pharmaceutical composition for the use of the present invention is provided in sterile form.

Preferably, the pharmaceutical composition for use according to the present invention are substantially free of water, substantially free of a preservative and are effective in inhibiting microbial growth.

Preferably, the pharmaceutical composition for use according to the present invention form small droplets (drops), in the range of about 8-12 µl more preferably about 10-12 µl, even more preferably about 11-12 µl, most preferably about 11 µl, when administered from a drop dispenser. This distinguishes the compositions of the present invention from the 0.05% cyclosporine aqueous (o/w) emulsions, that are characterized by droplet sizes of about 28.5 µl.

In a preferred embodiment, the composition for use is topically administered to a subject suffering from uveitis, such anterior uveitis or posterior uveitis, as single droplets having a volume of about 8-12 µl, more preferably of about 10-12 µl, even more preferably of about 11-12 µl, most preferably as droplets having a volume of about 11 µl.

Preferably, the pharmaceutical composition for use is topically administered to the eye of a subject suffering from uveitis, such as anterior uveitis or posterior uveitis, as a daily dose of 4 to 240 µg cyclosporine per eye, preferably as a daily dose of 4 to 60 µg cyclosporine per eye, more preferably as a daily dose of 16 to 240 µg cyclosporine per eye, most preferably as a daily dose of 8 to 120 µg cyclosporine per eye.

In a further preferred embodiment, the pharmaceutical composition for use is topically administered to the eye of a subject suffering from uveitis, such as anterior uveitis or posterior uveitis, as a daily dose of 4 to 48 µg cyclosporine per eye, preferably as a daily dose of 4 to 12 µg cyclosporine per eye, more preferably as a daily dose of 16 to 48 µg cyclosporine per eye, most preferably as a daily dose of 8 to 24 µg cyclosporine per eye.

Preferably, the pharmaceutical composition for use is topically administered to the eye of a subject suffering from uveitis, such as anterior uveitis or posterior uveitis, as a daily dose of 4 to 32 µg cyclosporine per eye, preferably as a daily dose of 4 to 6 µg cyclosporine per eye, more preferably as a daily dose of 16 to 32 µg cyclosporine per eye, most preferably as a daily dose of 8 to 16 µg cyclosporine per eye.

Preferably, the pharmaceutical composition for use is topically administered to the eye of a subject suffering from uveitis, such as anterior uveitis or posterior uveitis, as a daily dose of 8 to 48 µg cyclosporine per eye, preferably as a daily dose of 8 to 12 µg cyclosporine per eye, more preferably as a daily dose of 32 to 48 µg cyclosporine per eye, most preferably as a daily dose of 16 to 24 µg cyclosporine per eye.

In a further preferred embodiment, the pharmaceutical composition for use is topically administered to the eye of a subject suffering from uveitis, such as anterior uveitis or posterior uveitis, as a daily dose of 5 to 24 µg cyclosporine per eye, preferably as a daily dose of 5 to 6 µg cyclosporine per eye, more preferably as a daily dose of 20 to 24 µg cyclosporine per eye, most preferably as a daily dose of 10 to 12 µg cyclosporine per eye.

Preferably, the pharmaceutical composition for use is topically administered to the eye of a subject suffering from uveitis, such as anterior uveitis or posterior uveitis, as a daily dose of 10 to 48 µg cyclosporine per eye, preferably as a daily dose of 10 to 12 µg cyclosporine per eye, more preferably as a daily dose of 40 to 48 µg cyclosporine per eye, most preferably as a daily dose of 20 to 24 µg cyclosporine per eye.

It is also preferred, that the pharmaceutical composition for use is topically administered to the eye of a subject suffering form uveitis, such as anterior uveitis or posterior uveitis, up to four times per day, preferable the composition is administered three times per day, even more preferred the composition is topically administered twice per day or the composition is topically administered once per day.

Preferably, the pharmaceutical composition for use is topically administered to the eye of a subject suffering from uveitis, such as anterior uveitis or posterior uveitis, as a single dose of 4 to 60 µg cyclosporine per eye, preferably as a single dose of 4 to 12 µg cyclosporine per eye, more preferably as a single dose of 4 to 6 µg cyclosporine per eye, even more preferably as a single dose of 8 to 12 µg cyclosporine per eye, most preferably as a single dose of 5 to 6 µg, or as a single dose of 10 to 12 µg.

It is also preferred, that the pharmaceutical composition for use is topically administered to the eye of a subject suffering from uveitis, such as anterior uveitis or posterior uveitis, once per day as a single dose of 4 to 60 µg cyclosporine per eye, preferably once per day as a single dose of 4 to 12 µg cyclosporine per eye, more preferably once per day as a single dose of 4 to 6 µg cyclosporine per eye, even more preferably once per day as a single dose of 8 to 12 µg cyclosporine per eye, most preferably once per day as a single dose of 5 to 6 µg, or once per day as a single dose of 10 to 12 µg. Alternatively the pharmaceutical composition for use is topically administered to the eye of a subject suffering from uveitis, such as anterior uveitis or posterior uveitis, twice per day as a single dose of 4 to 60 µg cyclosporine per eye, preferably twice per day as a single dose of 4 to 12 µg cyclosporine per eye, more preferably twice per day as a single dose of 4 to 6 µg cyclosporine per eye, even more preferably twice per day as a single dose of 8 to 12 µg cyclosporine per eye, most preferably twice per day as a single dose of 5 to 6 µg, or twice per day as a single dose of 10 to 12 µg. Further preferred, the pharmaceutical composition for use is topically administered to the eye of a subject suffering from uveitis, such as anterior uveitis or posterior uveitis, four times per day as a single dose of 4 to 60 µg cyclosporine per eye, preferably four times per day as a single dose of 4 to 12 µg cyclosporine per eye, more preferably four times per day as a single dose of 4 to 6 µg cyclosporine per eye, even more preferably four times per day as a single dose of 8 to 12 µg cyclosporine per eye, most preferably four times per day as a single dose of 5 to 6 µg, or four times per day as a single dose of 10 to 12 µg.

It is preferred, that the pharmaceutical composition for use comprising 0.1% (w/v) cyclosporine dissolved in 1-perfluorobutylpentane is topically administered to the eye of a subject suffering from uveitis, such as anterior uveitis or posterior uveitis, twice per day as a single dose of 8 to 12 µg cyclosporine per eye. It is further preferred, that the pharmaceutical composition for use comprising 0.1% (w/v) cyclosporine dissolved in 1-perfluorobutylpentane is topically administered to the eye of a subject suffering from uveitis, such as anterior uveitis or posterior uveitis, twice per day as a single dose of 10 to 12 µg cyclosporine per eye.

It is preferred, that the pharmaceutical composition for use comprising 0.05% (w/v) cyclosporine dissolved in 1-perfluorobutylpentane is topically administered to the eye of a subject suffering from uveitis, such as anterior uveitis or posterior uveitis, twice per day as a single dose of 4 to 6 µg cyclosporine per eye. It is further preferred, that the pharmaceutical composition for use comprising 0.1% (w/v) cyclosporine dissolved in 1-perfluorobutylpentane is topically administered to the eye of a subject suffering from uveitis, such as anterior uveitis or posterior uveitis, twice per day as a single dose of 5 to 6 µg cyclosporine per eye.

It is preferred, that the pharmaceutical composition for use comprising or essentially consisting of 0.1% (w/v) cyclosporine dissolved in 1-perfluorobutyl-pentane, and optionally about 1.0% (w/w) of ethanol, is topically administered to the eye of a subject suffering from uveitis, such as anterior uveitis or posterior uveitis, twice per day as a single dose of 8 to 12 µg cyclosporine per eye. It is further preferred, that the pharmaceutical composition for use comprising or essentially consisting of 0.1% (w/v) cyclosporine dissolved in 1-perfluorobutylpentane, and optionally about 1.0% (w/w) of ethanol, is topically administered to the eye of a subject suffering from uveitis, such as anterior uveitis or posterior uveitis, twice per day as a single dose of 10 to 12 µg cyclosporine per eye.

It is preferred, that the pharmaceutical composition for use comprising or essentially consisting of 0.05% (w/v) cyclosporine dissolved in 1-perfluorobutyl-pentane, and optionally about 1.0% (w/w) of ethanol, is topically administered to the eye of a subject suffering from uveitis, such as anterior uveitis or posterior uveitis, twice per day as a single dose of 4 to 6 µg cyclosporine per eye. It is further preferred, that the pharmaceutical composition for use comprising or essentially consisting of 0.1% (w/v) cyclosporine dissolved in 1-perfluorobutylpentane, and optionally about 1.0% (w/w) of ethanol, is topically administered to the eye of a subject suffering from uveitis, such as anterior uveitis or posterior uveitis, twice per day as a single dose of 5 to 6 µg cyclosporine per eye.

As used herein, the term "consists" and related terms "consisting" or "consist" is to be understood as meaning that no other features, other than those prefaced by the term are present. In the context of pharmaceutical compositions, if any other constituent or component is present in the composition other than those prefaced by such term, then it is present only in trace or residual amounts such as to confer no technical advantage or relevance in respect of the object of the invention, such as may be further understood by the term "essentially" or "substantially" used in conjunction with these terms (e.g. 'essentially consisting of').

The use of a pharmaceutical composition as described in any one of the above embodiments in the manufacture or preparation of a medicament or a medicine for the treatment of a subject in need thereof in relation to any one of preferred uveitis conditions described herein are also provided for in the context of the present invention.

Further provided for within the context of the present invention, are also methods of treating subjects diagnosed with, and/or suffering from said uveitis conditions as described herein, wherein the methods may comprise the topical administration, such as by direct topical instillation to the eye, of any one of the defined compositions, preferably in any one of the described doses or amounts, and/or over any one of the defined periods for therapy.

All the preferred embodiments described above in relation to the pharmaceutical composition for the use of the present invention apply to the use of the pharmaceutical composition for the manufacture or preparation of a medicament or a medicine for the treatment of a subject suffering from uveitis.

Said treatment methods and compositions for therapeutic use are moreover preferably targeted towards human subjects diagnosed and/or suffering from uveitis.

In yet a further aspect, the invention provides also a kit comprising a pharmaceutical composition for use according to the invention and any of the embodiments described above, wherein the kit comprises a container for holding the pharmaceutical composition and a drop dispenser adapted for administering about 8 to 12 µl volume of the composition per drop.

In a further embodiment, the drop dispenser may be adapted for administering about 10-12 µl of the composition per drop, preferably 11-12 µl of the composition per drop, more preferably 11 µl of the composition per drop.

As understood herein, the drop dispenser may be a dispenser or applicator means which may be mounted, fixed or connected to the container for holding the pharmaceutical composition. Preferably, the drop dispenser is adapted for dispensing a single dose in the form of a single drop of the composition. More preferably, the drop dispenser is adapted for dispensing a single dose of 8- to 12-µl volume, preferably 10 to 12 µl, even more preferably 11 to 12 µl, most preferably a single dose of about 11-µl volume.

The container for holding the pharmaceutical composition as understood herein is preferably of a volume which may hold a single dose, but more preferably of a volume which may hold multiple or a plurality of doses of the composition. In an embodiment of the invention, the container of the kit may hold up to 160 doses of the pharmaceutical composition for use according to the present invention.

The container and/or the drop dispenser preferably may be manufactured from a thermoplastic material or polymer. In a one embodiment, the container and/or drop dispenser is manufactured from a thermoplastic material selected from polyethylene and polypropylene.

In one particular embodiment, the drop dispenser is manufactured from a polyethylene material, preferably selected from low density polyethylene and high density polyethylene, and more preferably is manufactured from a high-density polyethylene. In another embodiment, the container is manufactured from a polypropylene or polyethylene material, and more preferably is manufactured from polypropylene.

In yet a further embodiment, the invention relates to a kit comprising a pharmaceutical composition for use according to the invention, the kit comprising a container for holding the pharmaceutical composition and a drop dispenser adapted for administering about 8 to 12 µl per drop, preferably 10-12 µl, more preferably 11-12 µl, wherein the container is manufactured from polypropylene and wherein the drop dispenser is manufactured from a polyethylene selected from a low density polyethylene and a high density polyethylene, preferably a high density polyethylene.

Preferably, the container has a volume, or an interior space which is at least partially filled with a pharmaceutical composition for use according to the invention. In a further embodiment, the ratio of the volume of the pharmaceutical composition in the container to the total volume of the container is between 0.4 and 0.7. The total volume of the container, as understood herein refers to the total interior volume formed by the interior dimensions of the container. The volume of the pharmaceutical composition in the container refers to the fill volume, i.e. the volume of the pharmaceutical composition held in the container. For example, in a kit comprising a container with a total volume of 3.0 mL, it is preferred that the container holds a volume of 2.0 mL of a pharmaceutical composition according to the invention. Here, the ratio of the volume of the pharmaceutical composition in the container to the total volume of the container would be about 0.7.

Particularly preferred are kits comprising a pharmaceutical composition for use in accordance with the present invention, wherein the kit comprises, in addition to a drop dispenser adapted for administering about 8 to 12 µl per drop, any one of the following:
  about 2.0 mL of the pharmaceutical composition filled in a 3.0 mL volume container (i.e. a respective ratio of about 0.7); or
  about 2.0 mL of a pharmaceutical composition filled in a 5.0 mL volume container (i.e. a respective ratio of about 0.4); or
  about 2.5 mL of a pharmaceutical composition filled in a 5.0 mL volume container (i.e. a respective ratio of about 0.5).

Also preferred is a kit comprising a pharmaceutical composition for use in accordance with the present invention, wherein the kit comprises a container for holding the pharmaceutical composition and a drop dispenser adapted for administering about 8 to 12 µl per drop and wherein the ratio of the volume of head space in the container to the volume of the pharmaceutical composition is between 0.5 to 1.5. As understood herein, the volume of head space (or head space volume) in the container refers to the interior volume of the container, formed by the interior dimensions of the container which is not filled or occupied by the liquid pharmaceutical composition but which may contain atmosphere or inert gas.

For example, in a kit comprising a container holding a fill volume of 2.5 mL of a pharmaceutical composition for use according to the present invention, it is preferred that the head space volume available in the container is about 2.5 mL, wherein the ratio of the head space to pharmaceutical composition fill volume is about 1.0.

Particularly preferred are kits comprising a pharmaceutical composition for use in accordance with the present invention, wherein the kit comprises, in addition to a drop dispenser adapted for administering about 8 to 12 µl per drop, preferably about 10-12 µl per drop, more preferably 11-12 µl, most preferably 11 µl, any one of the following:
  a container holding about 2.0 mL of the pharmaceutical composition, wherein the container has about 1.0 mL volume of head space (i.e. a head space to fill volume ratio of about 0.5); or
  a container holding about 2.0 mL of the pharmaceutical composition, wherein the container has about 3.0 mL volume of head space (i.e. a head space to fill volume ratio of about 1.5); or
  a container holding about 2.4 mL of the pharmaceutical composition, wherein the container has about 2.6 mL volume of head space (i.e. a head space to fill volume ratio of about 1.1).

Such kits as provided in accordance with these embodiments may improve storage and dispensability (i.e., ease and consistency in dispensing) of the pharmaceutical compositions.

Further, the present invention comprises the following items 1 to 10, relating to a method for treating uveitis:
  1. A method of treating uveitis, the method comprising topically administering to an eye of a human suffering from uveitis or a disease or a condition related thereto a composition comprising about 0.05 to 0.5% (w/v) cyclosporine dissolved in 1-perfluorobutyl-pentane, wherein said method is therapeutically effective in treating uveitis or a disease or a condition related thereto in said human.
  2. A method of treating uveitis according to Item 1, wherein uveitis is anterior uveitis or posterior uveitis, preferably anterior uveitis.
  3. A method of treating uveitis according to any preceding items, wherein cyclosporine is present at a concentration of from about 0.1% (w/v) to 0.5% (w/v).
  4. A method of treating uveitis according to any preceding items, wherein cyclosporine is present at a concentration of from about 0.1% (w/v) to 0.3% (w/v).
  5. A method of treating uveitis according to any preceding items, wherein cyclosporine is present at a concentration of from about 0.05% (w/v) to 0.1% (w/v).
  6. A method of treating uveitis according to any of the preceding items, wherein the composition comprises ethanol.
  7. A method of treating uveitis according to item 6, wherein ethanol is present at a concentration of up to about 1.0% (w/w) based on the total weight of the composition.
  8. A method of treating uveitis according to any of the preceding items, wherein said composition consists of 0.05% to 0.5% (w/v) cyclosporine dissolved in a solution of about 99% (w/w) 1-perfluorobutyl-pentane and about 1.0% (w/w) ethanol.

9. A method of treating uveitis according to any preceding items, wherein said composition consists of 0.05% to 0.5% (w/v) cyclosporine dissolved in a solution of about at least 99% (w/w) 1-perfluorobutyl-pentane and up to about 1% (w/w) ethanol.

10. A method of treating uveitis according to any of items 1 to 6, wherein said composition further comprises up to about 0.5% (w/w) ethanol based on the total weight of the composition.

11. A method of treating uveitis according to item 10, wherein said composition consists of 0.05% to 0.5% (w/v) cyclosporine dissolved in a solution of about 99.5% (w/w) 1-perfluorobutyl-pentane and about 0.5% (w/w) ethanol.

12. A method of treating uveitis according to item 10, wherein said composition consists of 0.05% to 0.5% (w/v) cyclosporine dissolved in a solution of at least about 99.5% (w/w) 1-perfluorobutyl-pentane and up to about 0.5% (w/w) ethanol.

13. A method of treating uveitis according to any of the preceding items, wherein said composition consists of 0.1% to 0.5% (w/v) cyclosporine dissolved in a solution of about 99% (w/w) 1-perfluorobutyl-pentane and about 1.0% (w/w) ethanol.

14. A method of treating uveitis according to any of the preceding items, wherein said composition consists of 0.1% to 0.3% (w/v) cyclosporine dissolved in a solution of about 99% (w/w) 1-perfluorobutyl-pentane and about 1.0% (w/w) ethanol.

EXAMPLES

Example 1

An ex-vivo study with porcine eyes was performed in order to observe the distribution of cyclosporin in the tissues of the eye and compare the effect of the formulation on the distribution of cyclosporin (Ikervis® vs cyclosporin in F4H5 with and without ethanol). The study was performed as follows.

Formulations

In the study, the following formulations were tested: 1) Reference formulation: Ikervis®; 2) Test formulation 1: 0.1% Cyclosporine A in F4H5; 3) Test formulation 2: 0.1% Cyclosporine A in F4H5+1% w/w ethanol.

Ikervis® is an oil in water emulsion based on the Novasorb® technology.

TABLE 1

Ikervis ® emulsion

| Item | Description |
|---|---|
| Name | Cyclosporine A, 1 mg/ml, dissolved in MCT |
| CAS | 59865-13-3 |
| MW | 1202.61 g/mol |
| Batch | 5E16 |
| Concentration | 0.1% oil-in-water emulsion |
| Manufacturer | Santen GmbH |
| Supplier | By Novaliq GmbH via local pharmacy |
| Shelf life | December 2018 |

The test formulation 1 and test formulation 2 were prepared by dissolving Cyclosporine A (CAS 59865-13-3; Euticals GmbH) in F4H5 and F4H5 plus ethanol 1.0% w/w, respectively.

Study Design

Study arms and parallels: Each formulation was tested in four parallels (n=4) per incubation time point (0.5 h, 1 h, 2 h and 4 h) resulting in overall 48 single experiments on different eyes.

Dose per eye: 50 µL of each formulation was applied by means of a pipette onto the cornea.

Temperature: 32° C. (deviant from the corneal surface temperature of 34° C.)

Study evaluation: At the different time points, the tissues cornea (treated area), aqueous humor, vitreous humor, and retina were collected. All tissue samples were stored frozen at −80° C. until shipment. The tissues were analysed via RRLC-MS/MS. Deuterated internal standard CsA (from TRC Canada) was used. To each sample, 20 ml of IS (at 10 ng/20 ml) was spiked. Masses of individual tissue samples were recorded and used for further calculations.

Procedure

The pig eyes for the ex vivo experiment were received from the slaughterer (Odenwald-Schlachthof). The eyes were used within a few hours. Specifically, less than 3 hours after removal from the animal, the experiment was started. The pigs, from which the eyes were removed, were not treated with hot water, because this could damage the cornea.

The eyes were transported in cooled (4° C.) Hanks' Balanced Salt Solution (HBSS; VWR supplier; batch S15113L0612; composition with calcium, magnesium, sodium bicarbonate, without phenol red, sterile filtered). After they arrived at the laboratory, they were taken from the buffer and the connective tissue around the eye was removed. Also, the optic nerve was carefully removed with the scissors to place the porcine eye flat in a cavity of a six-well plate. Then the eyes were moistened with around 4 ml HBSS and covered with a petri dish (35×10 mm) to avoid water loss. The plate with the eyes was placed in a preheated oven (32° C., deviant from the corneal surface temperature of 34° C., and a bowl of water inside to ensure a constant saturated moisture) for about 5 minutes. After being taken out of the oven, they were moistened with 4 mL HBSS and polycarbonate corneal sleeves were placed on each cornea and fixed with tape to ensure a precise application of the test solution. 50 µl of the test or reference formulation, respectively, was applied by means of a pipette to the cornea sleeve opening and covered again with the petri dish.

A dose of 50 µl of each formulation was applied by means of a pipette to 3.14 cm² corneal surface. The applied HBSS was distributed very irregularly on the mentioned area and had to be regularly distributed with a pipette. Ikervis® in contrast was distributed more regularly on the cornea. The first drop of the suspension did not cover the entire area of the cornea, but a large part. After application of the whole volume, the suspension was distributed at the edge of the corneal sleeve. Due to the spreading behaviour of the SFAs, both cyclosporin test formulations were distributed regularly over the entire available area.

After the defined incubation time (0.5 h; 1 h; 2 h; 4 h) the eyes were rinsed with HBSS buffer to stop the penetration and placed in a new cavity filled with HBSS.

1) At each time point, aqueous humor was collected with a 22.5 gauge needle and placed in a vial. A parallel injection to corneal surface was applied. Maximum 150 µl sample was withdrawn.
2) The part of the cornea, which was in contact with the solution, was excised by means of scissors, rinsed with HBSS buffer, wiped dry and positioned in an Eppendorf vial.

3) The whole vitreous humor (around 2 ml) was collected in a petri dish (35×10 mm). After homogenization with a disposable syringe around 1 ml of the vitreous humor was transferred to a vessel.
4) The whole retina was collected with tweezers in a previously weighed vial.

All tissues were placed in previously weighed vials. After removal of the mentioned parts of the porcine eye at the defined times, the vials were weighed again, and the weights were noted. Additionally, the corresponding parts of 60 untreated eyes per matrix were removed as blank matrices for the bioanalytics. Finally, all samples were frozen at −80° C. until their shipment.

Visual Observation

Cyclosporine A was detected in the vitreous humour and in the retina. In the latter, an amount of cyclosporine A higher than 100 ng/g was found for both test formulations 1 and 2 at each incubation time point.

In a following study, cyclosporine A deriving from the test formulations was detected in the iris and in the ciliary body.

The invention claimed is:

1. A method of treating uveitis or a disease or condition associated thereto, the method comprising topically administering to an eye of a human suffering from uveitis or a disease or condition related thereto, a composition comprising cyclosporine at a concentration of from about 0.05% (w/v) to about 0.5% (w/v) dissolved in 1-perfluorobutyl-pentane.

2. The method according to claim 1, wherein the uveitis is anterior uveitis or posterior uveitis.

3. The method according to claim 1, wherein the uveitis is iridocyclitis or iritis.

4. The method according to claim 1, wherein the composition is essentially water-free and/or preservative free.

5. The method according to claim 1, wherein the cyclosporine is comprised at a concentration of from about 0.05% (w/v) to 0.1% (w/v) based on the total volume of the composition.

6. The method according to claim 1, wherein the composition comprises ethanol.

7. The method according to claim 6, wherein the ethanol is present at a concentration of up to 1.0% (w/w) based on the total weight of the composition.

8. The method according to claim 6, wherein the composition consists of cyclosporine at a concentration of from about 0.05 to about 0.1% (w/v), 1-perfluorobutyl-pentane and up to 1.0% (w/w) ethanol based on the total weight of the composition.

9. The method according to claim 6, wherein the cyclosporine is present at a concentration of 0.05% (w/v) and the ethanol is present at a concentration of 1.0% (w/w) based on the total weight of the composition.

10. The method according to claim 6, wherein the cyclosporine is present at a concentration of 0.1% (w/v) and the ethanol is present at a concentration of 1.0% (w/w) based on the total weight of the composition.

11. The method of claim 1, wherein the composition consists of 0.05% to 0.1% (w/v) cyclosporine in 1-perfluorobutyl-pentane.

12. The method according to claim 1, wherein the composition is topically administered to the eye of a subject suffering from uveitis as a single dose of about 4 to 60 μg cyclosporine per eye or wherein the composition is topically administered to the eye of a subject suffering from uveitis as a single dose of about 4 to 12 μg cyclosporine per eye.

13. The method according to claim 1, wherein the composition is topically administered to the eye of a subject suffering from uveitis as a daily dose of about 8 to 120 μg cyclosporine per eye or wherein the composition is topically administered to the eye of a subject suffering from uveitis as a daily dose of about 8 to 24 μg cyclosporine per eye.

14. The method according to claim 1, wherein the composition is administered as single droplets having a volume of about 8-12 μl or wherein the composition is administered as single droplets having a volume of about 10-12 μl or 11 μl.

15. The method according to claim 1, wherein the composition is administered up to four times per day or wherein the composition is administered twice per day.

16. The method according to claim 1, wherein the composition comprises or consists essentially of 0.1% (w/v) cyclosporine dissolved in 1-perfluorobutyl-pentane, and optionally up to 1% (w/w) ethanol, and wherein the composition is administered twice daily as a single dose of about 20 to 24 μg of cyclosporine per eye.

17. The method according to claim 1, wherein the composition comprises or consists essentially of 0.05% (w/v) cyclosporine dissolved in 1-perfluorobutyl-pentane, and optionally up to 1% (w/w) ethanol, and wherein the composition is administered twice daily as a single dose of about 10 to 12 μg of cyclosporine per eye.

* * * * *